US007425197B2

(12) United States Patent
Tzouriadou-Teske

(10) Patent No.: US 7,425,197 B2

(45) Date of Patent: Sep. 16, 2008

(54) METHOD AND A SYSTEM FOR TRANSFORMING A COMMON ROOM INTO A HEALING ENVIRONMENT

(76) Inventor: Elpida Tzouriadou-Teske, 48 Bouziki Street, Athens (GR) 11524

( * ) Notice: Subject to any disclaimer, the term of this patent is extended or adjusted under 35 U.S.C. 154(b) by 673 days.

(21) Appl. No.: 10/489,973

(22) PCT Filed: Oct. 24, 2002

(86) PCT No.: PCT/GR02/00056

§ 371 (c)(1),
(2), (4) Date: Mar. 18, 2004

(87) PCT Pub. No.: WO03/036593

PCT Pub. Date: May 1, 2003

(65) Prior Publication Data

US 2005/0007883 A1 Jan. 13, 2005

(30) Foreign Application Priority Data

Oct. 24, 2001 (GR) ............................ 20010100492

(51) Int. Cl.
*A61M 21/00* (2006.01)

(52) U.S. Cl. .......................................... 600/27; 600/26

(58) Field of Classification Search ..................... 600/1, 600/26–28; 160/10, 239
See application file for complete search history.

(56) References Cited

U.S. PATENT DOCUMENTS 4,641,446 A 2/1987 Jackson
5,676,633 A * 10/1997 August ........................ 600/27
6,250,798 B1 6/2001 Brainard et al.
2002/0198438 A1* 12/2002 Cromer et al. ................ 600/27

FOREIGN PATENT DOCUMENTS

| | | | |
|---|---|---|---|
| DE | 2243335 | A | 3/1973 |
| DE | 19729719 | A | 2/1998 |
| DE | 3925493 | A | 3/1998 |
| DE | 19830169 | A | 1/2000 |
| WO | WO 9819327 | A | 5/1998 |
| WO | WO 9942180 | A | 8/1999 |

* cited by examiner

*Primary Examiner*—Charles A. Marmor, II
*Assistant Examiner*—Christine D. Hopkins
(74) *Attorney, Agent, or Firm*—David A. Guerra

(57) ABSTRACT

Images that can have various subjects are formed by using the specific range of colors that the rainbow has. These images consist primarily of transparent, flexible, 3-D pictures which become even more beautiful when light is passed through them. Their size varies and they can be transferred from one surface to another, so they can be removed easily and leave the room exactly as it was before. They are accompanied: (a) by stories explaining the specific meanings of each color used in the picture and of each transfer from one color to the next; and (b) by other stimuli for the senses (audio-visual images, odors, tastes, etc. which try to give life to the theme of the image and give the viewer the sense that he or she is actually in the image). Their aim is to convert a negative space into a positive, and healing, one.

20 Claims, 6 Drawing Sheets

METHOD AND A SYSTEM FOR TRANSFORMING A COMMON ROOM INTO A HEALING ENVIRONMENT

CROSS-REFERENCE TO RELATED APPLICATIONS

This application is an U.S. national phase application under 35 U.S.C. §371 based upon co-pending International Application No. PCT/GR02/00056 filed on Oct. 24, 2002. Additionally, this U.S. national phase application claims the benefit of priority of co-pending International Application No. PCT/GR02/00056 filed on Oct. 24, 2002 and Greece Application No. 20010100492 filed on Oct. 24, 2001. The entire disclosures of the prior applications are incorporated herein by reference. The international application was published on May 1, 2003 under Publication No. WO 03/036593 A1.

BACKGROUND OF THE INVENTION

Field of the Invention

The aim of this invention is to change a plain, neutral or uninteresting room (where there are people affected by this negative environment) and, by using temporary means, to transform it into a positive, healing environment. Images can be formed in the room as following:

Description of the Prior Art

Pictures which are specially formed (see explanation below) are placed on transparent, translucent or mirror-like surfaces in the room, so that the user can see them often. The dynamic element of these structures is their texture (transparent), as well as the way one color, or material, interacts with its neighboring one.

Surfaces not suitable to host pictures can be changed by putting hidden colored light sources, and video or slide projectors, so that soft color light projections can be produced. These projections can accompany and compliment the pictures to create an aesthetic overall image in the room.

SUMMARY OF THE INVENTION

This invention isn't an improvement on a previous method, because it is addressed to a human need that only recently has been developed in high-tech, impersonal, environments (it has not yet been well understood by the majority). More and more researchers have proven that modern high-tech rooms as well as some modern artifacts (placed in these rooms for decoration) can create negative feelings to a patient and slow down the process of his or her recovery. There is already a tendency to plan new medical purpose-built facilities which look less threatening to a patient than the conventional ones. But how is it possible for the existing facilities to improve? How can patients (staying in a neutral, non-personal room during their recovery) be helped to feel more relaxed and cheerful? This invention is specifically addressed to each person that is hospitalized in such a depressing room; also to each hospital manager who cares to find a low-cost way to humanize existing hospital spaces until he or she can find the required capital to enable building a new, more human and less threatening, construction. This invention is also addressed to any person that feels trapped in the modern buildings of our civilization, any person that loves nature, but cannot bring it into the environment that he or she lives in (due to a variety of reasons).

The advantage of an image done in the way proposed by this method instead of using any other similar method is that it uses mainly rainbow transparent colors. It is common knowledge that a rainbow always gives pleasure to the eye of viewers and urges them to get well. From a psychological point of view, opaque colors represent all the unhealthy, unnecessary and unpleasant things which, the viewer wants to get rid of, while transparent rainbow colors and clear white sunlight represent the desirable progress from sickness to absolute health.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE PREFERRED EMBODIMENT

Figure 1:
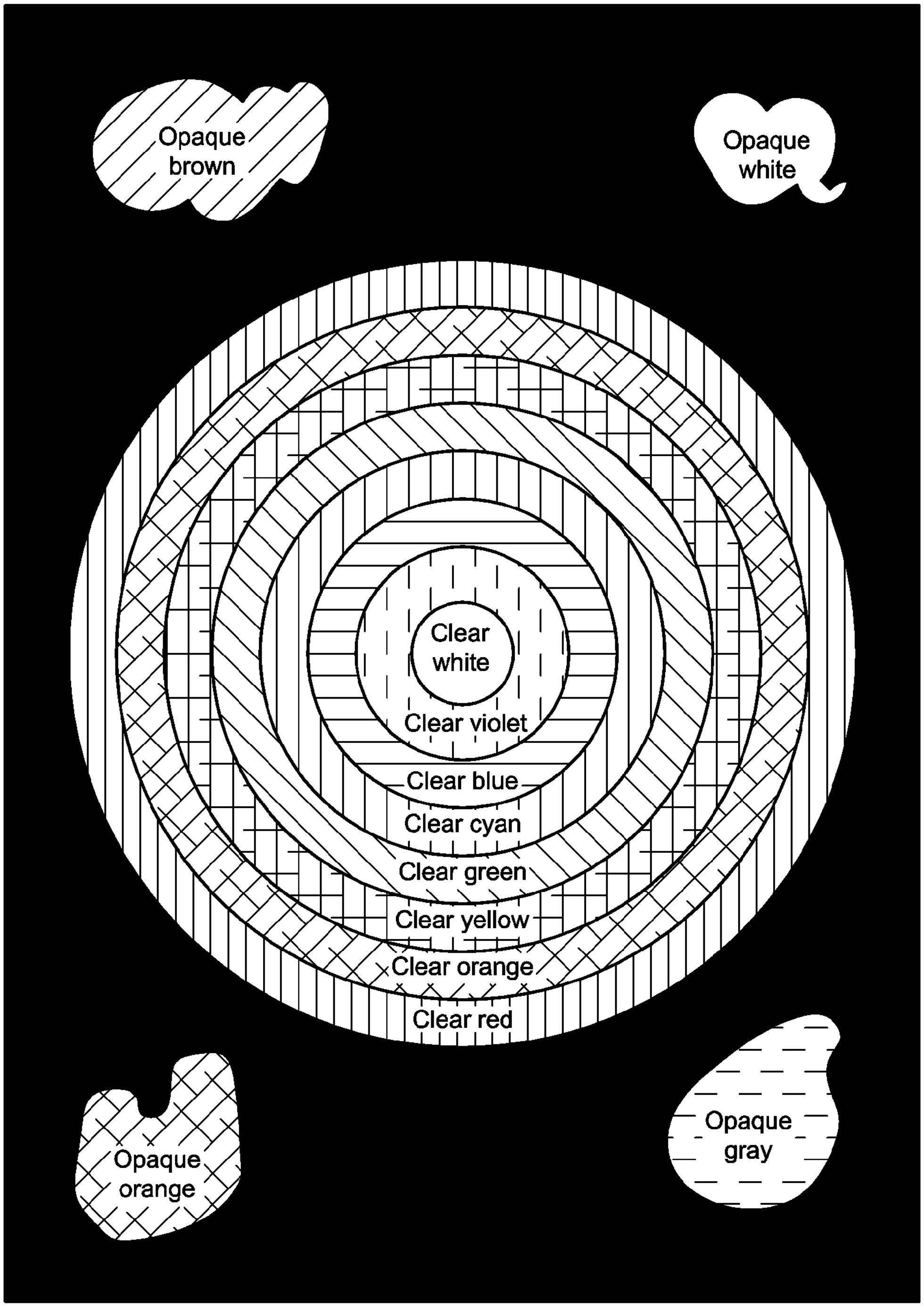
FIG. 1 is a front view of an embodiment of the method and a system for transforming a common room into a healing environment of the present invention.
Figure 2A:
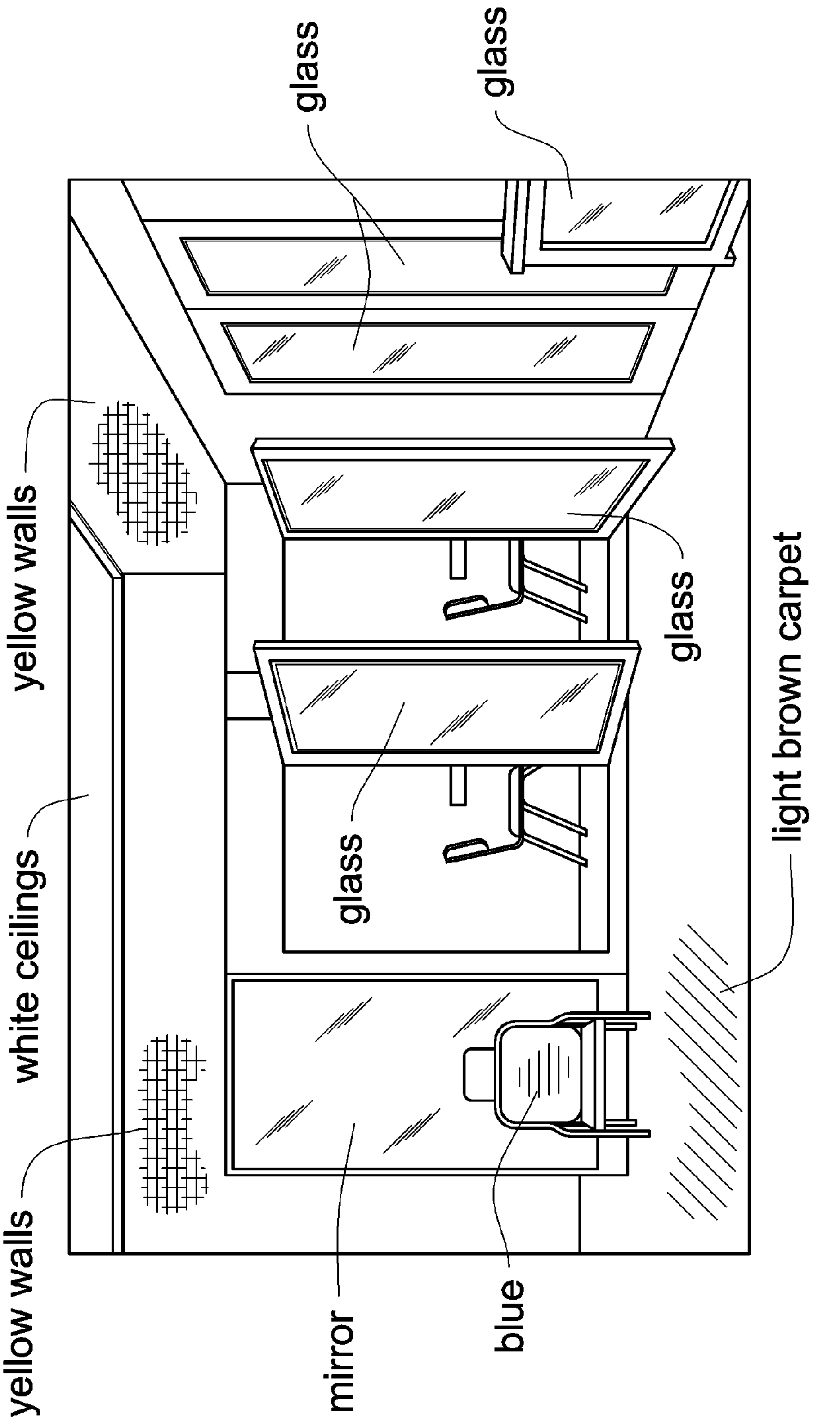
FIG. 2*a* is a perspective view of a room of the method and a system for transforming a common room into a healing environment of the present invention.
Figure 2B:
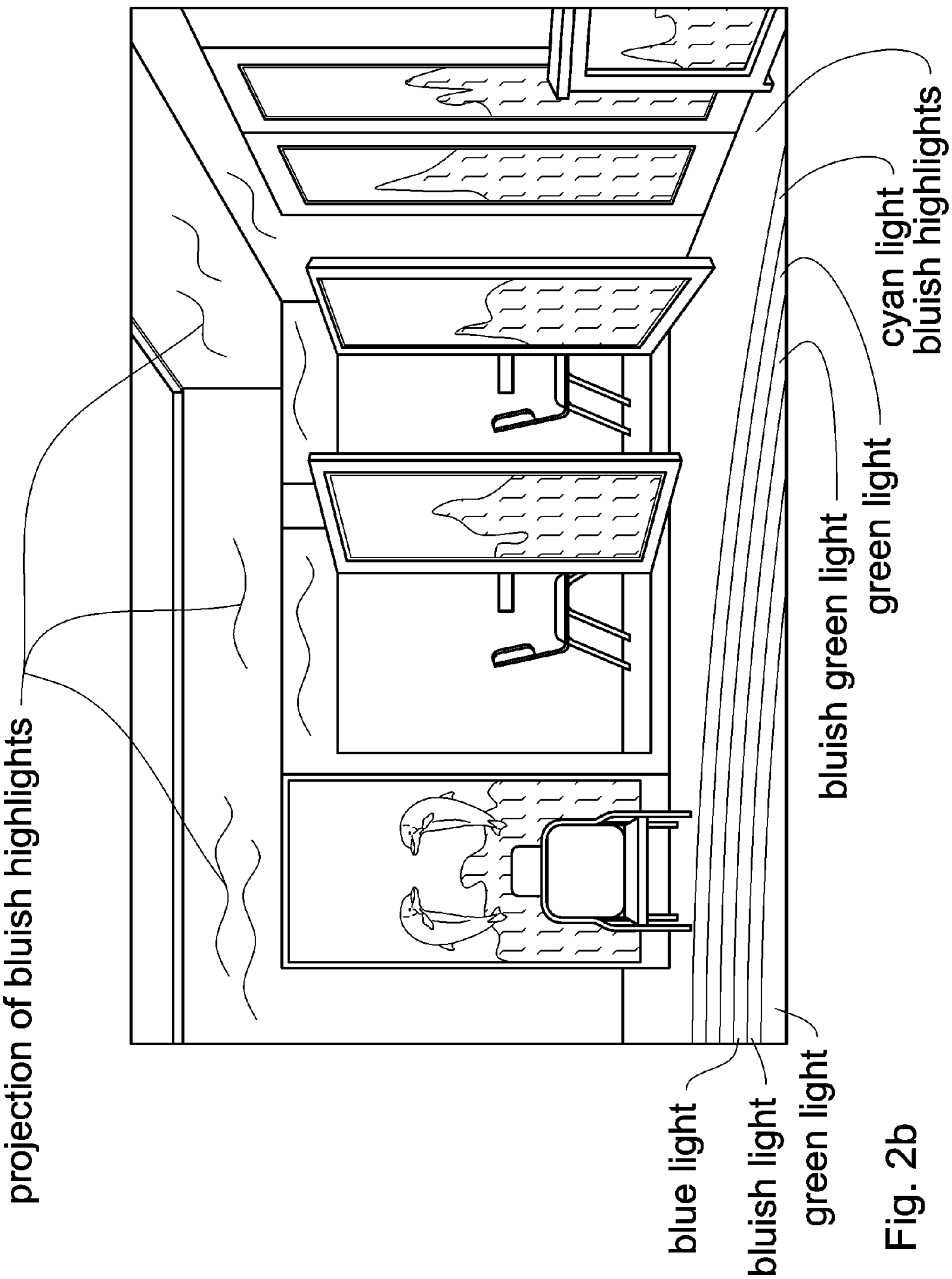
FIG. 2*b* is a perspective view of an alternate embodiment room of the method and a system for transforming a common room into a healing environment of the present invention.
Figure 2C:
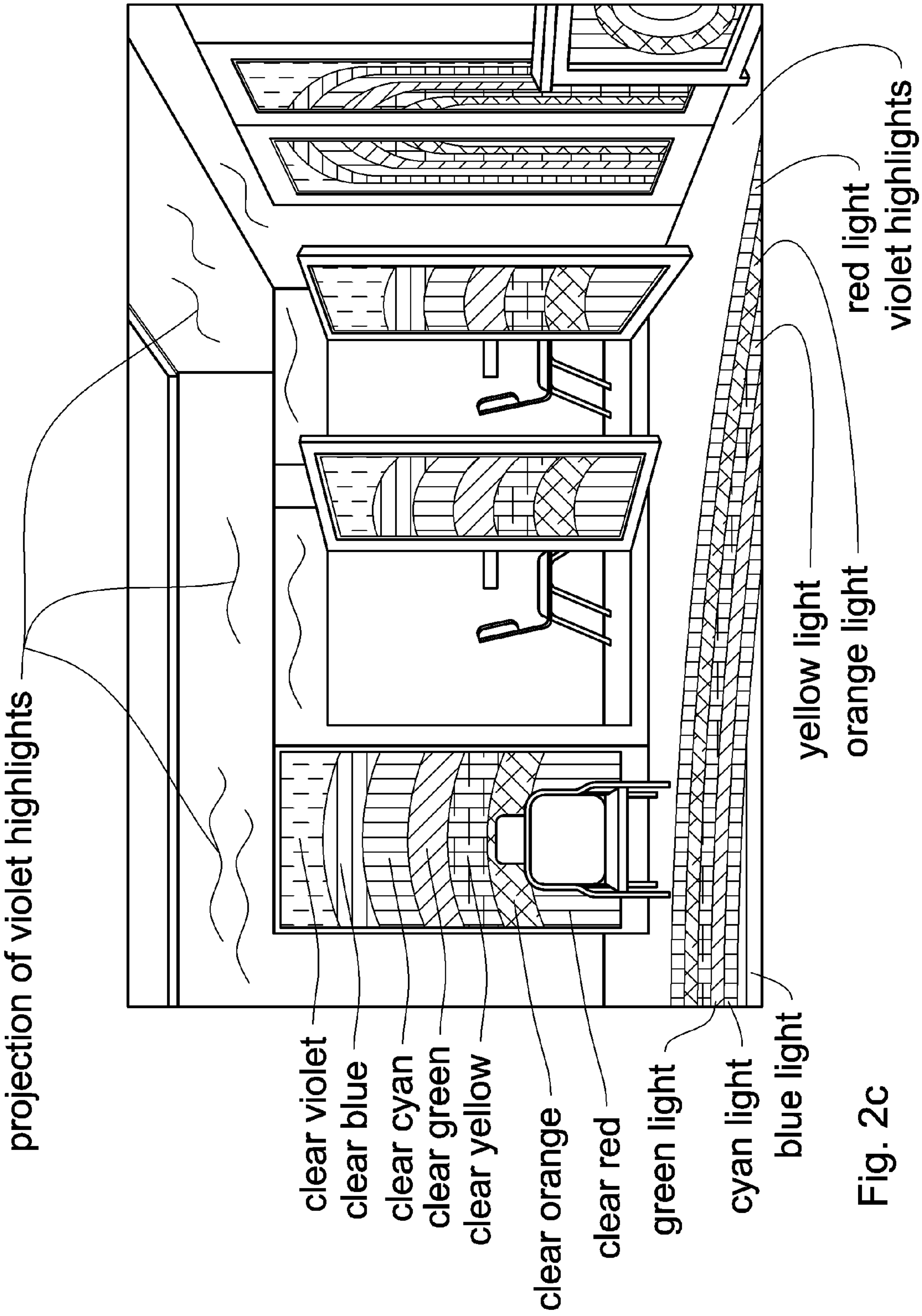
FIG. 2*c* is a perspective view of an alternate embodiment room of the method and a system for transforming a common room into a healing environment of the present invention.
Figure 3A:
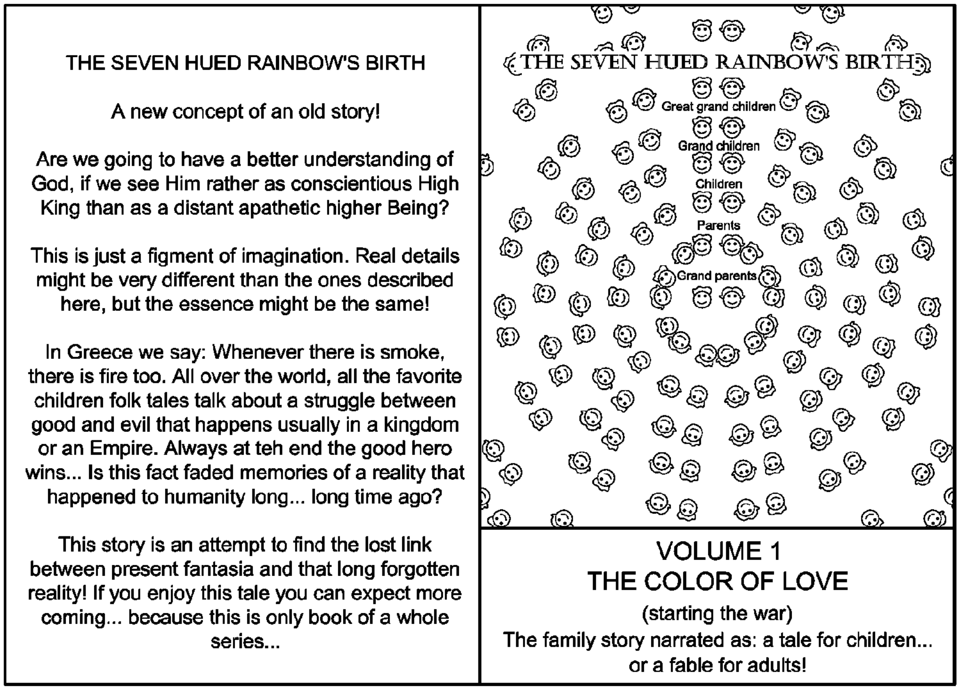
FIG. 3*a* is a front view of a paper book cover of the method and a system for transforming a common room into a healing environment of the present invention.
Figure 3B:
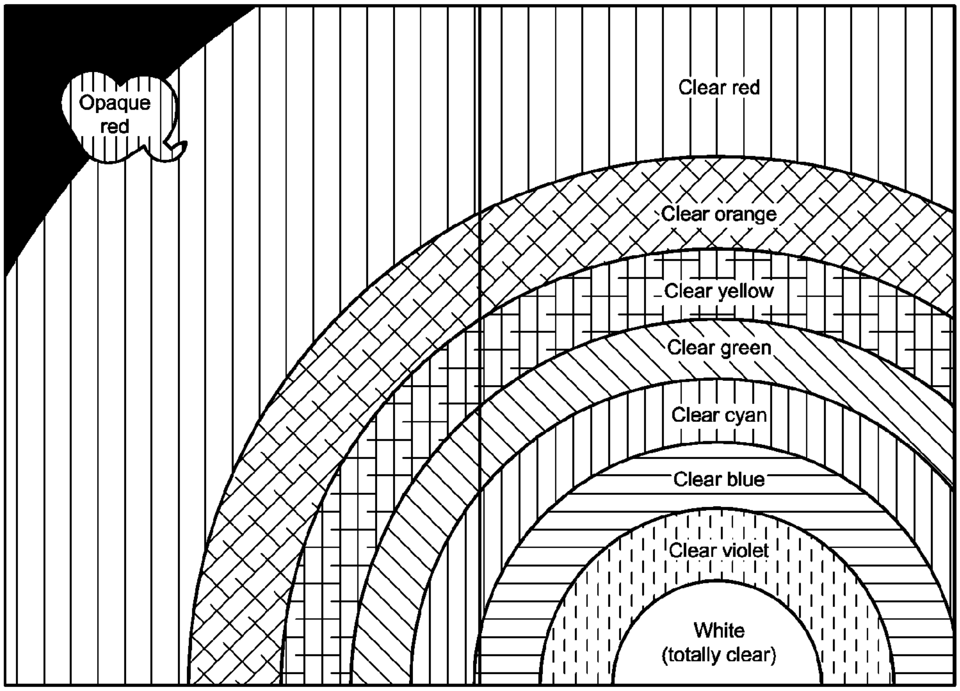
FIG. 3*b* is a back view of a painted plastic transparent sheet of the book cover of the method and a system for transforming a common room into a healing environment of the present invention.
Figures 4A, 4B:
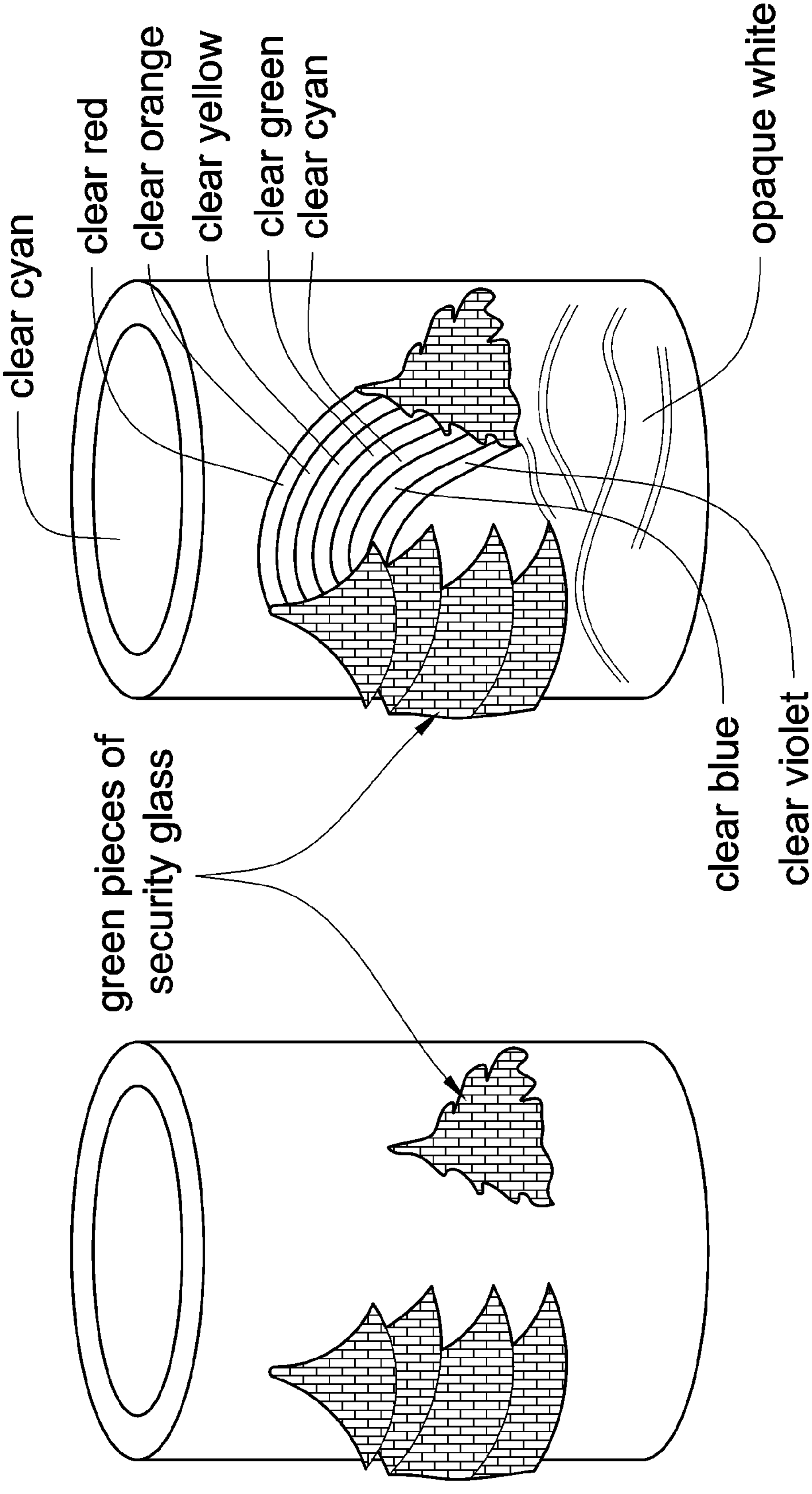
FIG. 4*a* is a perspective view of a vase of the present invention.
FIG. 4*b* is a perspective view of an alternate embodiment of the vase view of a painted plastic transparent sheet of the book cover of the present invention.

In a circular rainbow, surrounded by various opaque colors (see FIG. 1), the three outer rings of its seven colors (that is, the red, orange and yellow ring) are considered warm colors (which, psychologically, indicate the fight of a sick body against disease). The three inner rings with the cool colors (cyan, blue, violet) are the opposite of the warm colors. Being cool they prepare, psychologically, a patient to enjoy the peace that health brings after any victory over disease. Finally, for the poor patient who feels surrounded by threatening diseases (represented by the dark opaque area around the circular rainbow), this central bright and clear white area becomes an unexpectant, ideal escape towards a direction full of light, where dark disease doesn't dare to go! The middle green ring stands on its own, because it doesn't belong to either group of colors. Green is made by mixing a warm color (yellow) and a cool one (blue), so in a way it represents the gate through which someone can enter from the warm colors into the cool ones. It's interesting that, from a psychological point of view, we tend to consider green as a cool color and not as a warm one. So, we could say that the "peaceful" ring of cool colors is wider and richer in colors than the ring of warm ones. This gives a positive boost to a patient struggling for health.

These positive feelings can be reinforced by reading or listening to special stories accompanying the images and explaining what means for the spirit of the patient to be able to pass from one chromatic zone to the next. Also the rapid, and in-front of the viewer's eyes magic change of his/her immediate environment from negative to positive conveys the message that the sick body can be transformed into a healthy one as easily as it is done to the room! It's said that the environment is another layer of our own skin.

A necessary part of integrating these pictures is light which by interacting with their colors gives them life. Light can be natural or artificial. The best arrangement is when it comes from the opposite direction of the one that the viewer sees the picture, but it can come from any other direction (for example, there are special arrangements where the light comes from a hidden light source on the thin side of the glass, goes through the material and lights up only the inscriptions engraved in the glass, while the rest of the glass remains dark).

Whatever other means that can reinforce the liveliness of the overall image is also welcomed and strongly recommended. The aim is for the viewer to have the impression that he or she is in the picture, like in virtual reality scenes (computer techniques are included). For example:

A. An image about country-side scenery can be accompanied by:

1. sound tracked bird's singing, blowing wind, running water, etc.
2. real water running on a natural or artificial rock or on a glass surface. The water is collected and recycled through a small hidden pump. Also, local fog can be produced on a tiny water surface by means of a special ultrasound device.
3. breeze produced by hidden ionizers or fans which can distribute, in addition to fresh air, different odors relevant to the theme, such as wildflowers, cut grass, etc.
4. theatrical scenery techniques imitating natural scenes. (Let's assume that a patient desires to see open fire in a rural fireplace, but it is not permitted to light a real fire in the room. A device with light, wind and thin, silky material can be used to give the impression of a flickering flame.)

B. An image about a dream-like trip of a child-patient through the rainbow can be accompanied by:

1. machine-produced fog changing colors through the use of hidden lamps;
2. sound tracked noises of a trip in the universe or relevant stories presented in a form of radio theater.
3. flower bouquets in rainbow colors and their smells.
4. round lollipops having layers of colored caramel in the colors of the rainbow. As the child licks each layer, the next is revealed (the color of the room changes accordingly at the same time).
5. video games or virtual reality glasses with suitable programs (directed to create feelings of peace and security instead of anxiety).

Of course, in the process of creating all these images there is a general rule stating that means dangerous to health cannot be used, even if it makes the image more lively!

As mentioned previously, the theme of each image might vary widely, but the way of construction is always the same. There is a succession of 7 colors, exactly like the one that exists in the rainbow. The transparent colors cover the vast majority of the image, while there can be some dark, black or opaque colors in some small areas. Sometimes in some pictures there can be just one, or only a few colors, and not the whole range of them, because this specific picture is a part of a series which altogether presents the total succession of the rainbow colors. However, in all images the way of presentation will be identical, that is (starting from the lower or most insignificant part of the picture and moving up towards the center of the theme) the successive colors will be: black (or any other dark or opaque color), then transparent red, orange, yellow, green, cyan, royal blue, violet and white (totally transparent). Also, it is better for the chosen subject of the image to be something relating to nature. It has been proven that nature is extremely helpful in creating a positive healing environment.

The way of creating these pictures is basically the same, differentiated only by the creator's decision to construct it in one piece, or several pieces joined together. The material used for making these pictures allows this choice, but it requires:

1. To predetermine the sizes of the picture's parts.
2. to decide whether empty glass spaces are to be left in the pattern or not.
3. to calculate the thickness of the material of the various parts, and whether it can be removable or not.
4. to plan to put first the extra materials needed to give more "body" to the picture.

If the picture is portable and it has no borders between neighboring colors (this technique better represents the appearance of the actual rainbow with its uninterrupted colors) it has to be transferred altogether as a whole. It's more realistic to see a continuity of succession from one color to the next without obstacles or gaps. If there is a need for a cut, another place can be found in the picture, where neighboring colors aren't intermingling. This will depend on the specific picture and its concept, but there is always a solution (to cut the parts in a way so that the aesthetics of the overall design isn't damaged).

The special 3-D paints (used to make these pictures) have the following characteristics:

Initially they are in a liquid form, so they have to be applied on a horizontal, smooth, shiny surface. It's useful for this surface to be transparent because this facilitates the creator to copy the pattern which is placed underneath. When the paint is in liquid form it is opaque, so it is not easy to discern the pattern laid underneath. The maker has to organize his or her own job in such a way that each pattern will remain visible throughout the whole process of a picture's construction.

The freshly made picture needs to stay on a horizontal position undisturbed for several hours, while drying.

When it solidifies it makes a transparent, flexible, waterproof foil which has different thicknesses at different points, giving the impression of old-fashioned uneven glass. This foil can be removed from its base to be attached to any smooth surface—even a vertical one—without needing to use glue. The self-adhesive composition of the paint allows it to be removed from a surface and be put on an other, as often as needed without it losing its adhesive quality. It can, also, be applied to uneven surfaces because it is elastic and can change its shape slightly by pulling on it.

If there is a part of the finished composition that needs to be altered for some reason, it can be done very easily. The undesired part is cut away with an x-acto knife, and fresh paint can be applied to fill in the gap (after the whole part of the picture to be repaired is again in horizontal position). The new material blends with the old one. Only the edge of the cut might show, due to a difference in thickness, but even this can be mended by applying another layer. So actually, a picture that is done for a specific patient is never wasted! It can be used many times because it can be altered to fit the specific needs of another client. Archives of basic pictures can be developed accompanied by an index from which the client can choose a specific image which can then be modified according to the need.

Also, if a picture is made in parts, a change in the arrangement of the parts can result in a new picture altogether.

The colors of the picture, always, remain surprisingly bright and lively because they can be washed as often as needed. When someone cleans the glass, they are on, they are cleaned also (the pictures and the surface which they are applied on, behave like one solid thing, when they are washed with water). The material they are made of does not lose its elasticity and its color does not fade as some other stain glass imitations do (when time passes).

It won't make any difference if the picture is large or small. The way of construction can handle both, either large enough to cover a whole glass wall, or small enough to decorate a transparent page of a book or tiny glass artifacts. For example FIGS. (2$a$), (2$b$), (2$c$) shows how a common workshop (2$a$) can be transformed instantly into an image of underwater environment (2$b$) or a travel within a rainbow (2$c$). On the contrary FIG. (3$b$) is a small picture (fits the pages of a book). Specifically the image of FIGS. (3$a$) and (3$b$) is a double back and front cover of a book. The first layer (3$b$) is a transparent plastic sheet painted with transparent rainbow colors and the second (3$a$) is its regular paper cover. This extra layer (3$b$) with its colored reflections gives more life to the whole appearance of the book. Letters opaque or transparent (in opposing colors to the ones of the surrounding area) can be added on the transparent cover according to the need. Also the trasparent sheet could be a page or a part of a page inside the book and not just its cover. In such a case the appearnce of the picture will be somehow like the one of FIG. (1) or (4$b$) (only in relation to the technique used to distinguish between an opaque area of a page and a trasnparent one).

Of course, if we apply this invention on transparent plastic pages we cannot use the 3-D paints that we use for making the large pictures, because they are sticky, when enclosed in pages of a book. There are two solutions to this problem: either we paint the picture with the 3-D paints on a plastic sheet and we cover it with another transparent plastic sheet (like the one in FIG. 1) or we paint with conventional transparent paints (like the one in FIG. (3$b$) able to be reproduced by machines).

It is very important the ability that the 3-D paints aquire to have a thickness changeable from place to place in the picture. As a result the viewer gets a more appealing view than the one he or she gets by looking at a picture painted with other stained glass imitation paints (which usually form only a thin, even layer, and can't give any extra "body" to the glass).

If the picture needs to be even more three-dimensional than the one succeeded with the paint material, little pieces of glass or other light, transparent, material can be used to form a part of the picture. They are kept in their right place by the adhesiveness of the paint. This saves money because they fill the place that was meant to be filled by the more expensive paint material. Sometimes the picture can be formed using only little pieces of glass and transparent glue which will glue them on the glass base without using any paint. Especially valuable for such a use are broken securit glasses (like those used for car windows). These pieces, although small and independent from one another, stay together as their borders fit perfectly with each other. So, although they are separate, they is can be handled as a whole. They form an uneven glass sheet which is very interesting aesthetically and is also more flexible than an unbroken glass surface. As you can see in FIGS. (4$a$), (4$b$), a simple, clear, cylindrical vase can be transformed into an artifact by adding some fragments of broken green tinted windshield (made of securit glass). In FIG. (4$a$) the pieces of green glass are glued with transparent glue without using any paint, while in FIG. (4$b$) there is, also, transparent paint gluing together the little pieces of broken glass.

Another advantage of a picture made with the proposed special paints, as opposed to the conventional stained glass method is that these paints do not need the metallic strips that are necessary to hold the different pieces of glass together. The creator can put them in, or omit them, according to his/her wanting to give a stained glass impression or not; to form definite borders between neighboring colors or leave them to intermingle freely; to combine them with other light, transparent or opaque, small items or leave them plain. The final product will be like a real rainbow which is a play of colored light, sometimes mixed with clouds or other objects. It's an advantage that these pictures do not necessarily need to have an opaque strip of metallic joint that always exists in a stained glass work. This gives freedom to the creator to more accurately imitate the succession of rainbow colors than he/she could do, in case of working with the traditional stained glass technique. Pictures made with the proposed method look more realistic because the actual rainbow colors are the reflections of colored light intermingling freely at their borders and taking the shape of every object, they are projected on.

"In reality a rainbow contains thousands of different combinations and shades of the three primary colors; but the way that people perceive these colors is different (influenced by their culture mainly). The traditional way is to recognize seven distinct hues in the rainbow (the ones mentioned above). Nowadays people tend to recognize only six distinct hues (3 primary colors and 3 secondary ones). This paper goes along with the traditional way of dividing the rainbow into seven hues . . . because of a very important reason! A six-hued rainbow contains two equal zones of warm and cool colors, (representing sickness and health) each having exactly the same width! Because the war-like colors of the first zone are warm and vivid, usually they make a stronger impression than the peaceful ones of the second zone. So the mind tends to incline to the war-area of sickness than the peace-area of health! On the contrary a seven-hued rainbow has its middle on the green color . . . . It's interesting that—although green is made of one warm and one cool color and must be neutral—it is allied with the cool colors, because of its blue ingredient . . . . Blue is the only cool color of the three primary and it's such a strong color that defeats the other primary color, the warm yellow! Consequently in the seven-hued rainbow the "peace and health" zone has 4 colors and the "war and sickness" zone only 3! This makes the 7-hued rainbow to move towards health dynamically. The viewer sees a small war-area and a bigger peace-area and this is promising and encouraging".

The invention claimed is:

1. A method for producing a temporary, scenic environment, supportive of health care, in a room, said method comprising the steps of:

(a) providing panels made of transparent or translucent material surrounded by a frame including a source of light, said panels being adapted to receive pictures made of transparent materials which creates an impression of stained-glass, said panels being attachable to parts of a room;

(b) providing thin panels made of a substrate, able to receive pictures made of transparent materials which creates an impression of stained-glass, said thin panels being attachable to parts of said room;

(c) providing pictures having a transparent main surface, and transparent or translucent and opaque materials placed on some small parts of said main surface, wherein said materials are paints;

(d) providing additional pictures, as described above in step (c), said additional pictures having an extra body of transparent material located under a transparent main surface that gives them depth created by small pieces of glass inserted between said transparent main surface and said substrate of said thin panels;

(e) projecting colored light on parts of said room by means of a projector;

(f) producing acoustic stimulants;

(g) diffusing odors relevant to said pictures and said additional pictures that have been created in said room;

(h) creating a breeze, localized fog, running water recycled through a pump and artificial flame;

(i) determining to use said thin panels on the parts of said room in cases where limited room space prohibits the use of said panels; and (j) determining to use said pictures or said additional pictures to produce a scenic environment, then attaching said pictures or additional pictures to said panels determined from step (i);

wherein said running water is created by pumping water over rocks in a recycling cycle using said pump, and said artificial flame is created by illuminating a silky material with a light.

2. The method according to claim 1, wherein said projected colored light in step (e) is a succession of black, red, orange, yellow, green, cyan, blue, violet, and white.

3. The method according to claim 1, wherein said fog is created on a small water surface by an ultrasound device.

4. The method according claim 1, wherein said breeze is created from an ionizer.

5. The method according to claim 1, wherein said breeze is created from a fan.

6. The method according to claim 1, wherein said light source of said panels in step (a) is located on the side of said panel in said frame.

7. The method according to claim 1, wherein step (c) further comprises the step of laying said transparent main surface out horizontally, placing said paint on top of said transparent main surface to produce said pictures with different thicknesses, allowing said paint to dry and solidify to form a flexible film, and removing said film from said transparent main surface and attaching it to at least one of said panels.

8. The method according to claim 7, wherein said step (c) further comprising the step of forming pieces of glass corresponding to parts of said pictures, and securing said formed pieces of glass to said paint section representing said parts of said pictures.

9. The method according to claim 1, wherein said room is a health care room.

10. A method for producing a temporary, scenic environment, supportive of health care, in a room, said method comprising the steps of:

(a) providing at least one panel having a transparent or translucent material surrounded by a frame including a source of light, said panel being adapted to receive pictures made of transparent materials, said panel being attachable to parts of a room;

(b) providing at least one thin panel having a substrate, said thin panel being able to receive pictures made of transparent materials, said thin panel being attachable to parts of said room;

(c) providing at least one picture having a transparent main surface, and transparent or translucent and opaque materials placed on some small parts of said main surface, wherein said materials are paints;

(d) laying said transparent main surface of said picture out horizontally;

(e) placing said paints on top of said transparent main surface to produce said at least one picture, wherein said paints are placed on said transparent main surface with different thicknesses;

(f) allowing said paint to dry and solidify to form a flexible film;

(g) removing said film from said transparent main surface and attaching it to one of said panels;

(h) providing at least one additional picture, as described above in steps (c-g);

(i) positioning additional pieces of said transparent material under said flexible film in said additional picture from step (h), wherein said additional pieces of transparent material are small pieces of glass;

(j) projecting colored light in a succession of black, red, orange, yellow, green, cyan, blue, violet, and white lights on parts of said room by means of a projector;

(k) producing acoustic stimulants; (l) diffusing odors relevant to said at least one picture and said at least one additional picture that have been created in said room;

(m) creating a breeze, localized fog, running water recycled through a pump of a surface, and an artificial flame;

(n) determining to use said thin panels on parts of said room in cases where limited room space prohibits the use of said panels; and (o) determining to use said at least one picture or said at least one additional picture to produce a scenic environment, then attaching said at least one picture or at least one additional picture to said panels determined from step (n).

11. The method according to claim 10, wherein said fog is created on a small water surface by an ultrasound device.

12. The method according claim 10, wherein said breeze is created from an ionizer.

13. The method according to claim 10, wherein said breeze is created from a fan.

14. The method according to claim 10, wherein said light source of said panels in step (a) is located on the side of said panel in said frame.

15. The method according to claim 10, wherein said running water is created by pumping water over rocks in a recycling cycle using said pump, and said artificial flame is created by illuminating a silky material with a light.

16. The method according to claim 10, wherein said step (e) further comprises the step of forming pieces of glass corresponding to parts of said picture, and securing said formed pieces of glass to said paints on said transparent main surface.

17. The method according to claim 10, wherein said room is a hospital room.

18. A method for producing a temporary, scenic environment, supportive of health care, in a room, said method comprising the steps of:

(a) providing at least one panel having a transparent or translucent material surrounded by a frame including a source of light, said panel being adapted to receive a picture, said panel being attachable to parts of a room;

(b) providing at least one thin panel having a substrate, said thin panel being able to receive a picture thereon, said thin panel being attachable to parts of said room;

(c) providing at least one picture having a transparent main surface, and transparent or translucent and opaque materials placed on some small parts of said main surface, wherein said materials are paints;

(d) laying said transparent main surface of said picture out horizontally;

(e) placing said paints on top of said transparent main surface to produce the desired picture, wherein said paints are placed on said transparent main surface with different thicknesses;

(f) forming pieces of glass corresponding to parts of said picture in step (e), and securing said formed pieces of glass to said paints on said transparent main surface;

(g) allowing said paint to dry and solidify to form a flexible film;

(h) removing said film from said transparent main surface and attaching it to one of said panels;

(i) providing at least one additional picture, as described above in steps (c-h);

(j) positioning additional pieces of said transparent material under said flexible film in said additional picture from step (i), wherein said additional pieces of transparent material are small pieces of glass;

(k) projecting colored light in a succession of black, red, orange, yellow, green, cyan, blue, violet, and white lights on parts of said room by means of a projector;

(l) producing acoustic stimulants;

(m) diffusing odors relevant to said at least one picture and said at least one additional picture that have been created in said room;

(n) creating a breeze, localized fog, running water recycled through a pump of a surface, and an artificial flame;

(o) determining to use said thin panels on parts of said room in cases where limited room space prohibits the use of said panels; and (p) determining to use said at least one picture or said at least one additional picture to produce a scenic environment, then attaching said at least one picture or at least one additional picture to said panels determined from step (o).

19. The method according to claim 18, wherein said fog is created on a small water surface by an ultrasound device, said light source of said panels in step (a) is located on the side of said panel in said frame, said running water is created by pumping water over rocks in a recycling cycle using said pump, and said artificial flame is created by illuminating a silky material with a light.

20. The method according to claim 18, wherein said room is a health care room.

* * * * *